United States Patent [19]

Raff et al.

[11] Patent Number: 4,756,885
[45] Date of Patent: Jul. 12, 1988

[54] MEASURING SENSOR FOR DETERMINING THE OXYGEN CONTENT IN GASES

[75] Inventors: Lothar Raff, Remseck; Helmut Weyl, Schwieberdingen; Hans-Martin Wiedenmann, Stuttgart, all of Fed. Rep. of Germany

[73] Assignee: Robert Bosch GmbH, Stuttgart, Fed. Rep. of Germany

[21] Appl. No.: 852,807

[22] PCT Filed: Jul. 4, 1985

[86] PCT No.: PCT/DE85/00229
§ 371 Date: Feb. 21, 1986
§ 102(e) Date: Feb. 21, 1986

[87] PCT Pub. No.: WO86/00709
PCT Pub. Date: Jan. 30, 1986

[30] Foreign Application Priority Data

Jul. 6, 1984 [DE] Fed. Rep. of Germany ... 8420216[U]
Mar. 30, 1985 [DE] Fed. Rep. of Germany ....... 3511730

[51] Int. Cl.$^4$ .............................................. G01N 27/56
[52] U.S. Cl. ..................................... 422/98; 204/428; 338/277
[58] Field of Search .......................... 422/98; 204/428; 60/270; 338/34, 229, 230, 233, 277

[56] References Cited

U.S. PATENT DOCUMENTS

| | | | |
|---|---|---|---|
| 3,835,012 | 9/1974 | Hemak | 204/428 |
| 3,891,529 | 6/1975 | Beesch | 204/428 |
| 3,960,692 | 6/1976 | Weyl et al. | 204/428 |
| 4,442,420 | 4/1984 | Novak | 338/34 |

FOREIGN PATENT DOCUMENTS

| | | |
|---|---|---|
| 2338536 | 4/1974 | Fed. Rep. of Germany . |
| 8101584 | 6/1981 | Fed. Rep. of Germany . |
| 2030304 | 4/1980 | United Kingdom . |

Primary Examiner—David L. Lacey
Attorney, Agent, or Firm—Michael J. Striker

[57] ABSTRACT

A combination of a measuring sensor and protector having a measuring sensor with a housing and having an elongated cup-like protective pipe engaged with the housing. The pipe has a bottom having a convex shape with an inlet opening. The pipe also has at least one outlet opening spaced away from the bottom. A deflector extends inward from the pipe at an acute angle relative to a longitudinal axis of the pipe and away from the bottom so that when gas flows longitudinally within the pipe from the inlet opening, the gas is deflected by the deflector to flow around the deflector to the at least one outlet opening. The bottom also has a boss-like bulging portion projecting outward to form the inlet opening so as to reduce contamination of the measuring element by preventing solid particles in the gas from entering inside the pipe.

23 Claims, 1 Drawing Sheet

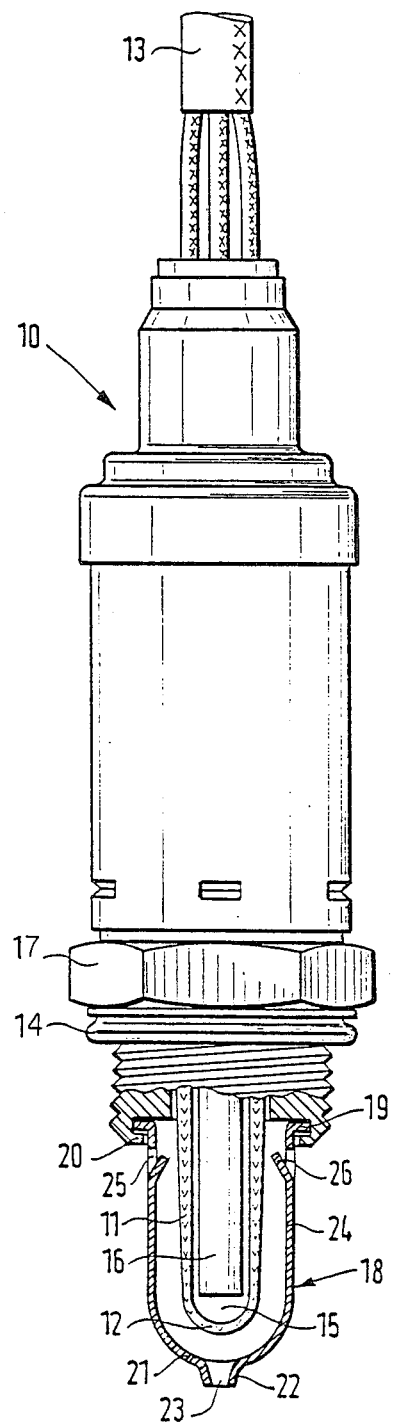

MEASURING SENSOR FOR DETERMINING THE OXYGEN CONTENT IN GASES

BACKGROUND OF THE INVENTION

The invention is based on a measuring sensor for determining the oxygen content in gases. A measuring sensor is already known (DE-PS 23 38 536) which is provided with a protective pipe which encompasses, a segment of a measuring element (solid electrolyte pipe) essentially consisting of a ceramic material extending from a pipe-like metal housing. This protective pipe is provided with a plurality of openings at its side wall for the input of the measuring gases and a small opening in diameter, for the output of the measuring gases. The openings in the side wall of the protective pipe are so formed so that they essentially guide the measuring gases tangentially with respect to the inside face of the protective guide, and so that the measuring element is substantially protected against bombardment by the solid particles which are contained in the measuring gas.

SUMMARY OF THE INVENTION

The measuring sensor of the invention is advantageous in that due to a different guiding of the measuring gas to the measuring element and due to a specific design of the protective pipe, the contamination or poisoning (oil ashes, reaction product of the lead, metallic dust of motor valves and the like) of the measuring element is considerably reduced which contributes to a substantial increase in the life span. A further advantage is that the protective pipe prevents erroneous controls in non-representative measuring gas peaks due to the aforementioned characteristics and enables that the response time is the same for a high oxygen component reducing to a low oxygen content or vice versa, which simplifies the electronic gating circuit. In case that the measuring element is provided with a resistor heating element an energy saving is obtained because of this protective pipe.

BRIEF DESCRIPTION OF THE DRAWING

One exemplified embodiment of the invention is illustrated in the drawing and is explained in more detail in the following description. The drawing illustrates an enlarged side view of a measuring sensor, whereby the end segment of the measuring sensor is illustrated as a longitudinal section.

DESCRIPTION OF THE EXEMPLIFIED EMBODIMENT

The measuring sensor 10 illustrated in the drawing for determining the oxygen content in gases is in particular used in exhaust gases of internal combustion engines. The principle structure of such a measuring sensor 10 is already known from the German Patent No. 81 01 584. This measuring sensor 10 operates in accordance with the known principle of the oxygen concentration chain with ion conductive solid electrolytes; preferably stabilized cubic zirconium dioxide is used. In the present example the solid electrolyte is structured as a solid electrolyte pipe 11 which is provided with a bottom 12. We have not shown the layer like electrodes on the outer side and on the inner side of this solid electrolyte pipe 11 and also have not shown the protective layer of this electrode which is exposed to the measuring gases. These electrodes are preferably mounted on the solid electrolyte pipe 11 as porous layers and are connected with electrical connecting parts in a known manner, of which at least one electrically feeds into the connecting side cable 13; commonly the electrode which is disposed on the outer side of the solid electrolyte pipe 11 and which has a catalyzing effect is connected with the metal housing 14 which is applied to ground. A rod like resistor heating element 16 extends into the inner chamber 15 of the solid electrolyte pipe 11 essentially filling the inner chamber 15 and extending in close proximity of bottom 12 to the solid electrolyte pipe 11. In many applications of this measuring sensor 10, one does not require the arrangement of a resistor heating element 16. The inner chamber 15 of the solid electrolyte pipe 11 is exposed to a reference gas (for example air) which is in contact with the mentioned counter electrode, not illustrated. The remainder structure of this measuring sensor 10 corresponds substantially to the structure of the measuring sensor which is described in the German Patent No. 81 01 584; additionally illustrated is merely a packing ring 17 which is nondetachably mounted on metal housing 14.

The segment of the solid electrolyte pipe 11 which extends from the metal housing 14, is provided with a cuplike protective pipe 18, which preferably consists of a corrosion resistant steel sheet metal. This protective pipe 18 is provided on its open end segment with an outwardly extending flange 19 which is shaped as a corrugated disk and is mounted on the front face of the metal housing 14 by means of a flanged edge 20. The protective pipe 18 encompasses the solid electrolyte pipe 11 is spaced therefrom and has a bottom 21 which is formed as a convex cupola. At the farthest extending area of this cupola like bottom 21, a boss like convex bulging 22 is provided which preferably is formed frustrum like and tapers. This bulging 22 is provided with an opening 23 to permit the input of the measuring gases. This opening has a diameter of 2.5 mm but, depending on the type of application, it may have a diameter of between 1 and 4 mm, preferably of 2 to 3 mm. The bulging 22 which encompasses the opening has a height of 1 mm but, depending on the type of application, it may have a height between 0.3 to 2 mm, preferably of 0.4 to 1.5 mm. The height of the cupola like bottom 21 is 4 mm but, depending on the type of application, may be between 2.5 and 6 mm, preferably between 3 and 5 mm. The total length of such a protective pipe 18 is 20 mm but, depending on the type of application, it may be between 12 and 30 mm, preferably between 18 and 25 mm.

For the discharge of the measuring gases from the inner chamber of the protective pipe 18, six openings 25 are provided in the sidewall 24 of the protective pipe 18 which are disposed in the proximity of the end of metal housing 14 and thereby have a distance from this end of metal housing 14 of less than 5 mm, preferably of 1.5 to 3 mm; in the present example this distance is 2 mm. The free cross section of these openings 25 in the sidewall 24 of the protective pipe 18 is preferably so dimensioned that its height is 0.5 mm and its width 2 mm. Depending on the type of application, these openings 25 may vary in their free cross section, that is, 0.3 mm height by 1 mm width and 1 mm height and 3 mm width. The number of these openings 25 may, depending on the type of application, be between 3 and 9, preferably between 4 and 6. Preferably, these openings 25 are disposed in the side wall 24 of this protective pipe 18 in one single plane extending transversely to the longitudinal axis of the protective pipe 18.

Together with the bulging 22, which in its center contains the opening 23 for the gas inlet, the arrangement and design for the deflection means 26 is of importance for the advantageous effect of this protective pipe 18, which returns the measuring gases discharging from openings 25 at an acute angle to the longitudinal axis of the protective pipe 18. These deflection means 26 are preferably reeved into the side wall 24 of the protective pipe 18 and are bent. These plate like deflection means 26 extend with their free ends into the inner chamber of the protective pipe 18 and are substantially directed to the end section of the measuring sensor. The bulging 22, which is provided in the bottom 21 of the protective pipe 18 provides that solid particles in the measuring gas cannot enter the inner chamber of the protective pipe 18. These aforedescribed deflection means 26 on the opening 25, which serve for the discharge of the gas, provide for and support the advantages of bulging 22, in particular the already described advantages with respect to eliminating of erroneous controls and the simplification of the electronic gating circuit. The small cross sections of openings 23 and 25 and the obtained lower measuring gas amount which flows through the protective pipe 18 also provides a lower heating capacity in such measuring sensor 10 which contain in the inner chamber 15 of its solid electrolyte pipe 11 a heat resistor element 16.

Not only the aforedescribed solid electrolyte pipe 11 with bottom 12 etc. may be used as a measuring element for a measuring sensor 10 in accordance with the invention, but also measuring elemnts with different configuration (for example, platelet like as in U.S. Pat. Nos. 4,011,655; 4,283,261) or other modes of operations (for example, resistor or change in conductivity as in U.S. Pat. Nos. 4,007,435; 4,011,655); all of these measuring elements are solid bodies.

We claim:

1. A combination of a measuring sensor and protector for determining an oxygen content in gases having solid particles, in particular for exhaust gases of internal combustion engines, the combination comprising:
    a measuring sensor including a housing with an open end and an elongated measuring element having a first portion bounded by the housing and a second portion extending through the open end, the second portion having an element end spaced furthest from the open end of the housing;
    said protector positioned and arranged for protecting the second portion of the measuring element from the gas to be determined for oxygen content and including an elongated cup-like protective pipe with a pipe end engaging the open end of the housing, said pipe forming a chamber, said chamber accomdating said second portion, said pipe having a longitudinal axis and a bottom portion arranged furthest away from said pipe end; and
    said protector including means for guiding the gas through said chamber and including an inlet opening in said pipe communicating with said chamber at said bottom portion, at least one outlet opening in said pipe communicating with said chamber and spaced away from said bottom portion, and deflection means extending inward from said pipe at an acute angle relative to said longitudinal axis of said pipe and away from said bottom portion so that when the gas flows longitudinally through said chamber from said inlet opening, the gas is deflected by said deflection means to flow around said deflection means to said at least one outlet opening, said bottom portion having a convex shape and having a boss-like bulging portion projecting outward and forming said inlet opening so as to reduce contamination of the measuring element by solid particles by preventing solid particles in gases from entering said chamber.

2. The combination in accordance with claim 1, wherein said at least one outlet opening comprises a plurality of outlet openings, said outlet openings being disposed in proximity to said pipe end.

3. The combination in accordance with claim 2, wherein said outlet openings are spaced a distance of less than 5 mm from said pipe end.

4. The combination in accordance with claim 3, wherein said openings are spaced a distance between 1.5 and 3 mm inclusive from said pipe end.

5. The combination in accordance with claim 2, wherein said outlet openings (25) having a height between 0.3 mm and 1.0 mm inclusive and a width between 1 mm and 3 mm inclusive.

6. The combination in accordance with claim 2, wherein the protective pipe (18) consists of a metallic material.

7. The combination in accordance with claim 2, wherein each of said outlet openings (25) having a height of 0.5 mm and a width of 2 mm.

8. The combination in accordance with claim 1, wherein the protective pipe (18) consists of a metallic material.

9. The combination in accordance with claim 1, wherein the protective pipe (18) has a total length of 12 to 30 mm.

10. The combination in accordance with claim 1, wherein the inlet opening (23) in the bottom (21) of protective pipe (18) has a diameter of 1 to 4 mm.

11. The combination in accordance with claim 1, wherein the boss like bulging (22) of the protective pipe (18) has a height of 0.3 to 2 mm.

12. The combination in accordance with claim 11, wherein the bulging (22) of the protective pipe (18) has a convex shape.

13. The combination in accordance with claim 1, wherein said bottom portion has a cup-like shaped part with a height of between 2.5 and 6 mm inclusive.

14. The combination in accordance with claim 1, wherein said protective pipe (18) has a total length between 18 mm and 25 mm inclusive.

15. The combination in accordance with claim 1, wherein said inlet opening (23) in the bottom (21) of said protective pipe (18) has a diameter between 2 and 4 mm inclusive.

16. The combination in accordance with claim 1, wherein said bulging portion (22) has a height between 0.4 and 1.5 mm inclusive.

17. The combination in accordance with claim 1, wherein said deflecting means has a free end extending into said chamber, said member being formed as a reeved and bent plate.

18. The combination in accordance with claim 1, wherein said at least one outlet opening comprises between 3-9 inclusive outlet openings.

19. The combination in accordance with claim 18, wherein said outlet opening are aligned in a single plane extending transversely to said longitudinal axis of said protective pipe.

20. The combination in accordance with claim 18, wherein the number of said outlet openings is between 4 to 6 inclusive.

21. The combination in accordance with claim 1, wherein said pipe end includes an outwardly directed mounting flange (19).

22. The combination in accordance with claim 21, wherein said flange has a corrugated disc-like profile.

23. The combination in accordance with claim 1, wherein said bulging portion has the shape of a frustum.

* * * * *